US00PP15711P3

(12) United States Plant Patent
Perkins

(10) Patent No.: US PP15,711 P3
(45) Date of Patent: Apr. 5, 2005

(54) *ANGELONIA* PLANT NAMED 'CART DEPINK'

(50) Latin Name: *Angelonia angustifolia*
Varietal Denomination: Cart Depink

(75) Inventor: Ralph Tyler Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 250 days.

(21) Appl. No.: 10/400,087

(22) Filed: Mar. 25, 2003

(65) Prior Publication Data

US 2004/0194179 P1 Sep. 30, 2004

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Jondle & Associates P.C.

(57) ABSTRACT

An *Angelonia* cultivar particularly distinguished by deep pink color flowers, compact habit and good basal branching.

1 Drawing Sheet

Genus and species: *Angelonia angustifolia.*
Variety denomination: 'Cart Depink'.

BACKGROUND OF THE NEW PLANT

The present invention comprises a new and distinct cultivar of *Angelonia,* botanically known as *Angelonia angustifolia,* and hereinafter referred to by the cultivar name 'Cart Depink'. The new cultivar is asexually reproduced from vegetative cuttings and tissue culture resulting from the cross of the seed/pod parent 00-F18-2, a pink proprietary line that is unnamed and unpatented×00-F20-3, a deep purple proprietary line that is unnamed and unpatented.

'Cart Depink' is a product of a planned breeding program intended to create new *angelonia* plants with deep pink colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new *Angelonia* plant is illustrated by the accompanying photograph which shows blooms, buds, and foliage of the plant in full color, the colors shown being as true as can be reasonably obtained by conventional photographic procedures. The photograph was taken in late summer. The 4–5 month old plant was cut from stock plants in late December, rooted and potted into a 4 inch pot and grown in a lexan covered green house until the end of April. They were then acclimatized for 2 weeks in a covered hoop and planted in the field for summer field trials.

The Photograph shows the mature inflorescence.

DESCRIPTION OF THE NEW CULTIVAR

The following detailed descriptions set forth the distinctive characteristics of 'Cart Depink'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 supplemental light and color readings were taken in the greenhouse in the winter season under natural light. Plants had been cut back numerous times prior to data readings taken. All major branches are cut back about 10–20 cm to keep them on-flowering and the plant from becoming unruly. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.—Angelonia angustifolia.*
*Commercial.—Angelonia.*
Form: Upright and erect.
Growth and branching habit: Good vigorous habit, well branched, pinching 1–2 times after transplant enhanced branching.
Height: From soil level to top of blooms: Approximately 40–55 cm.
Width: Approximately 30–50 cm including flowers.
Time to produce a finished flowering plant: 8–10 weeks for a 4–6 inch pot.
Outdoor plant performance: Full sun, free-flowering through the summer, some heat tolerance. Use in mixed container plantings or mass planting in a bed.
Time to initiate roots: Approximately 18–23 days at warm temperatures.
Root description: Fibrous, free branching.

THE LEAVES

Arrangement: Opposite.
Length: 4.8–5.2 cm.

Width: 1.0–1.1 cm.
Leaf blade shape: Linear.
Leaf margin: Serrate.
Apex shape: Acute.
Base shape: Cuncate.
Mature leaf color: Upper side; RHS 147A (yellow-green); Underside, RHS 137B (green) with RHS 145C (yellow-green) mid-vein.
Juvenile leaf color: Upperside between RHS 143A & B; Underside, closest to RHS 144A, but greener.
Texture: Many short glandular hairs, few with a yellow-green hue, physically leaving a sticky residue.
Venation: Pinnate.
Venation color: RHS 145A (yellow-green).

THE STEM

Length: 40–50 cm from base of plant to tip of branch.
Diameter: 0.3–0.4 cm taken from the lower ⅓ of the stem.
Internodes length: 1.2–2.5 cm.
Branch aspect: 45–60 degree.
Color: RHS 143A (green).
Texture: Short glandular hairs, few with a yellow-green hue.
Stem anthocyanin: No.
Pedicel color: RHS 143A (green).
Pedicel length: 2.2–2.6 cm.
Pedicel diameter: 0.1 cm.
Pedicel texture: Many short glandular hairs, all with yellow-green hue.
Pedicel anthocyanin: Appearing irregularly.
Pedicel aspect: 45–60 degrees.

THE BUD

Shape: Orbicular.
Diameter: 0.5–0.7 cm.
Length: 0.5–0.9 cm.
Color at tight bud: RHS 144B (yellow-green) with a blush of RHS 36A (red) as it matures.

THE FLOWER

Blooming habit: Continuous throughout the growing season. Good floriferousness.
Floret and inflorescence type: Single, 2 lipped (5-petaled, fused at base) flowers, solitary or sometimes two in a leaf axis on a terminal raceme.
Flower color, upper side, upper lip/lower lateral petals: RHS 64D (red-purple) base color; Mid-petals: RHS# 64D (red-purple) base color with a spot of RHS 155B (white) and RHS 149B (yellow-green), basally.
Flower color, underside: RHS 63C (red-purple).
Corolla color inside: RHS 63C (red-purple) base color with spots of RHS N79B (purple).
Florets per raceme: 24–32.
Floret diameter: 2.7–2.9 cm.
Petal size, upper lip, 1 petal, and length: 0.7–0.8 cm from the corolla opening; width 1.0–1.1 cm.
Lower lip, lateral petal, and length: 0.9–1.0 cm from the corolla opening; width 1.1–1.2 cm.
Lower lip, mid-petal, length: 2.0–2.2 cm from ovary; width 1.0–1.1 cm.
Petal base: Fused.
Petal margin: Entire.
Petal texture: Papillose and some short glandular hairs, many with a yellow-green hue.
Petals base: Fused.
Petal margin: Entire.
Petal texture: Papillose, and some short glandular hairs, many with a yellow-green hue.
Sepals: 5, fused at base.
Sepal color: RHS 141A (green).
Sepal length: 0.3–0.4 cm.
Sepal width: 0.1 cm.
Sepal shape: Ovate.
Sepal apex: Acute.
Sepal anthocyanin: No.
Sepal texture: Many short glandular hairs all with a yellow-green hue.
Lastingness of individual blooms: 6–9 days.
Fragrance: None.

THE REPRODUCTIVE ORGANS

Stamens: 4, in pairs.
Filament color: RHS N155B (white).
Pollen color: RHS 160C (greyed-yellow).
Pollen amount: Moderate.
Pistil: One.
Stigma color: RHS N155B (white).
Style color: RHS N155B (white).
Fruit seed set: Not observed.

DISEASE AND INSECT RESISTANCE

Not observed.

COMPARISON WITH KNOWN CULTIVARS

'Cart Depink' differs from the female parent, 00-F18-2, in the following ways: 'Cart Depink' has a fuller, more upright and freer branching habit, larger flowers and is a deep pink colored flower and 00-F18-2 has a pink flower.

'Cart Depink' differs from the male parent, 00-F20-3 in the following ways: 'Cart Depink' has a fuller, more upright and freer branching habit, is more floriferous and has a deep pink colored flower and 00-F20-3 has a deep purple flower.

I claim:

1. A new and distinct *Angelonia* plant as shown and described herein.

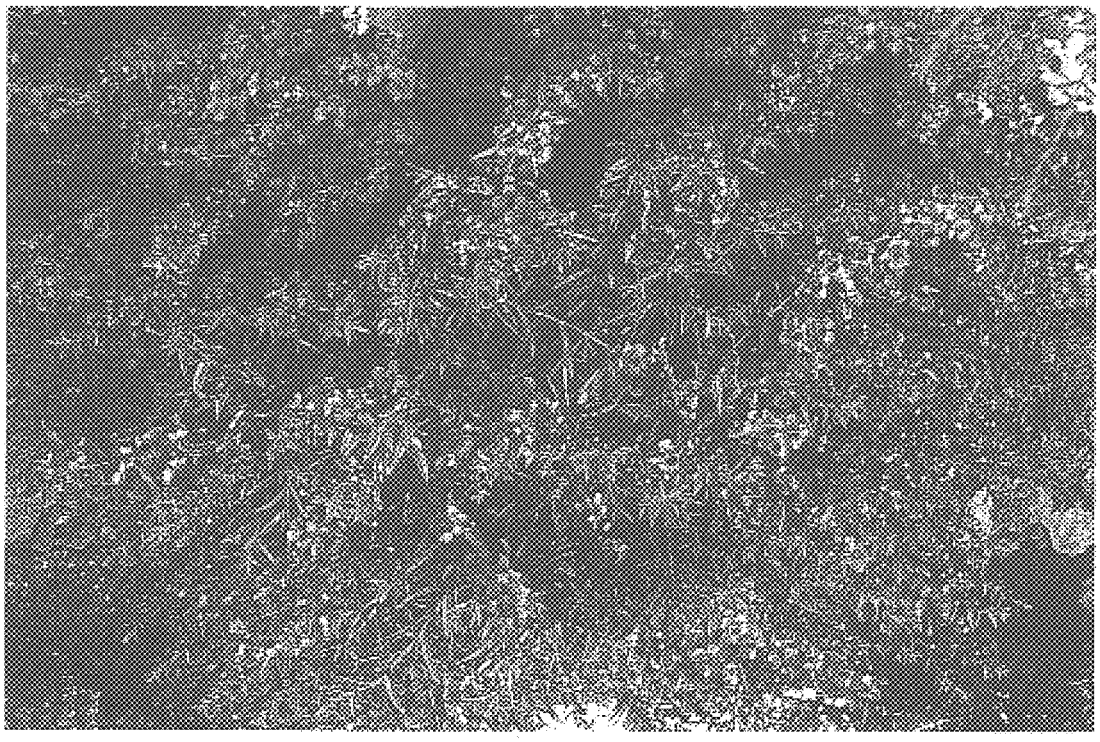

* * * * *